US007452861B2

(12) United States Patent
Kaniga

(10) Patent No.: US 7,452,861 B2
(45) Date of Patent: Nov. 18, 2008

(54) USE OF AN ECHINOCANDIN ANTIFUNGAL AGENT IN COMBINATION WITH A GLYCOPEPTIDE ANTIBACTERIAL AGENT

(75) Inventor: Koné Kaniga, Hayward, CA (US)

(73) Assignee: Theravance, Inc., South San Francisco, CA (US)

( * ) Notice: Subject to any disclaimer, the term of this patent is extended or adjusted under 35 U.S.C. 154(b) by 486 days.

(21) Appl. No.: 10/895,492

(22) Filed: Jul. 21, 2004

(65) Prior Publication Data

US 2005/0026819 A1 Feb. 3, 2005

Related U.S. Application Data

(60) Provisional application No. 60/489,173, filed on Jul. 22, 2003.

(51) Int. Cl.
*A61K 38/16* (2006.01)
*A61K 38/00* (2006.01)
*A61K 31/33* (2006.01)
*A01N 43/00* (2006.01)

(52) U.S. Cl. .............................. 514/8; 514/183; 514/9
(58) Field of Classification Search .................. None
See application file for complete search history.

(56) References Cited

U.S. PATENT DOCUMENTS

| | | | |
|---|---|---|---|
| 5,378,804 A | 1/1995 | Balkovec et al. | |
| 5,925,616 A | 7/1999 | Whittemore | |
| 6,107,458 A | 8/2000 | Ohki et al. | |
| 6,267,979 B1 * | 7/2001 | Raad et al. ................ | 424/405 |
| 6,635,618 B2 | 10/2003 | Leadbetter et al. | |
| 6,719,991 B2 * | 4/2004 | Darouiche et al. .......... | 424/422 |
| 6,743,777 B1 | 6/2004 | Burkhardt et al. | |
| 2003/0017975 A1 | 1/2003 | Ikeda et al. | |
| 2004/0242505 A1 | 12/2004 | Kaniga | |
| 2005/0026819 A1 * | 2/2005 | Kaniga ........................ | 514/8 |

FOREIGN PATENT DOCUMENTS

| | | |
|---|---|---|
| EP | 0 525 499 A1 | 2/1993 |
| EP | 0 667 353 A1 | 8/1995 |
| WO | WO 00/72865 A2 | 12/2000 |

OTHER PUBLICATIONS

Ge et al. Vancomycin Derivatives That Inhibit Peptidoglycan Biosynthesis Without Binding D-Ala-D-Ala. Sciene. Apr. 16, 1999. vol. 284, pp. 507-511.*
Giglione et al. The situation on antimicrobial agents and chemotherapy in 2002: Highlights of the 42nd ICAAC. Sep. 27-30, 2002, San Diego, USA.Expert Opin. Ther. Targets. 2002. vol. 6 No. 6, pp. 691-697.*
Boger. Vancomycin, Teicoplanin and Ramoplanin. Medicinal Research Reviews. 2001. vol. 21, No. 5, pp. 356-381.*
Arikan et al., "New agents for the treatment of systemic fungal infections-current status", Expert Opin. Emerging Drugs, 7(1), pp. 3-32 (2002).

Chiou et al., "Synergy, Pharmacodynamics, and Time-Sequenced Ultrastructural Changes of the Interaction between Nikkomycin Z and the Echinocandin FK463 against *Aspergillus fumigatus*", Antimicrobial Agents and Chemotherapy, vol. 45, No. 12, pp. 3310-3321 (2001).
Denning, "Echinocandins:a new class of antifungal", Journal of Antimicrobial Chemotherapy, 49, pp. 889-891 (2002).
Denning, "Echinocandin antifungal drugs", The Lancet, vol. 362, pp. 1142-1151 (2003).
Eliopoulos et al., "Antimicrobial Combinations", Antibiotics in Laboratory Medicine, 4th Edition, Williams & Wilkins, pp. 330-396 (1996).
Groll et al., "Caspofungin:pharmacology, safety and therapeutic potential in superficial and invasive fungal infections", Expert Opin. Investig. Drugs, 10(8), pp. 1545-1558 (2001).
Hossain et al., "New investigational antifungal agents for treating invasive fungal infections", Expert Opin. Invest. Drugs, 9(8), pp. 1797-1813 (2000).
Lewis et al., "Rationale for Combination Antifungal Therapy", Pharmacotherapy, vol. 21, No. 8, pp. 149s-164s (2001).
Manavathu et al., "Differential activity of triazoles in two-drug combinations with the echinocandin caspofungin against *Aspergillus fumigatus*", J. of Antimicrobial Chemotherapy, 51, pp. 1423-1425 (2003).
Nicolaou et al., "Chemistry, Biology, and Medicine of the Glycopeptide Antibiotics", Angew. Chem. Int. Ed., 38, pp. 2096-2152 (1999).
Shalit et al., "In Vitro Synergy of Caspofungin and Itraconazole against *Aspergillus* spp.: MIC versus Minimal Effective Concentration End Points", Antimicrobial Agents and Chemotherapy, vol. 47, No. 4, pp. 1416-1418 (2003).
Sugar, "Overview: Antifungal combination therapy", Current Opinion in Investigational Drugs, 2(10), pp. 1364-1365 (2001).
Vanden Bossche, "Echinocandins-an update", Expert Opin. Ther. Patents, 12(2), pp. 151-167 (2002).
Lacroix, C., et al., "Echinocandins: a new class of antifungal agents", *Medicine et maladies infectieuses*, 33(4):183-191, Apr. 2003. (in French with English abstract).
Link, H., "Antimicrobial prophylaxis and therapy in neutropenia", Mycoses 46(Suppl. 2):21-32, Feb. 2003. (in German with English abstract).

(Continued)

Primary Examiner—Cecilia J Tsang
Assistant Examiner—Marcela M Cordero Garcia
(74) Attorney, Agent, or Firm—Jeffrey A. Hagenah

(57) ABSTRACT

This invention is directed to methods of administering an echinocandin antifungal agent in combination with a glycopeptide antibacterial agent having a substituent comprising at least about 8 carbon atoms. The invention is also directed to methods of using an echinocandin antifungal agent in combination with a specified glycopeptide antibacterial agent to treat fungal infections; and to compositions, kits and systems comprising an echinocandin antifungal agent and a specified glycopeptide antibacterial agent.

9 Claims, No Drawings

OTHER PUBLICATIONS

Preobrazhenskaya, M. and Olsufyeva, E., "Patents on glycopeptides of the vancomycin family and their derivatives as antimicrobials: Jan. 1999-Jun. 2003", *Expert Opin. Ther. Patents*, 14(2):141-173, 2004.

Taccone F.S., et al., Caspofungin salvage therapy in a neutropenic patient with probable invasive aspergillosis: a case report, *Supportive Care in Cancer: Official Journal of the Multinational Association of Supportive Care in Cancer*, 11(11):742-744, Nov. 2003.

Kureishi et al., "Double-blind comparison of teicoplanin versus vancomycin in febrile neutropenic patients receiving concomitant tobramycin and piperacillin: Effect on cyclosporine A-associated nephrotoxicity", *Antimicrobial Agents and Chemotherapy*, vol. 35 No. 11, pp. 2246-2252 (Nov. 1991).

Pace, John L., "TD-6424: A novel multifunctional antibiotic", *Abstr Intersci Conf Antimicrob Agents Chemother*, 42: Abstract No. 614, Sep. 27-30, 2002.

Office Action in U.S. Appl. No. 10/854,575, dated Nov. 24, 2006.
Office Action in U.S. Appl. No. 10/854,575, dated Apr. 27, 2007.
Office Action in U.S. Appl. No. 10/854,575, dated Aug. 6, 2007.

* cited by examiner

USE OF AN ECHINOCANDIN ANTIFUNGAL AGENT IN COMBINATION WITH A GLYCOPEPTIDE ANTIBACTERIAL AGENT

CROSS REFERENCE TO RELATED APPLICATIONS

This application claims the benefit of U.S. Provisional Application No. 60/489,173, filed on Jul. 22, 2003; the entire disclosure of which is incorporated herein by reference in its entirety.

BACKGROUND OF THE INVENTION

1. Field of the Invention

This invention relates to the use of an echinocandin antifungal agent in combination with a glycopeptide antibacterial agent. More specifically, this invention relates to methods of using an echinocandin antifungal agent in combination with a glycopeptide antibacterial agent to treat fungal infections; and to compositions, kits and systems comprising an echinocandin antifungal agent and a glycopeptide antibacterial agent.

2. State of the Art

Echinocandin antifungal agents, such as caspofungin, micafungin and anidulafungin, are a relatively new class of therapeutic agents useful for treating fungal infections. Generally, such echinocandin antifungal agents have been found to have fewer side effects than, for example, polyene antifungal agents such as amphotericin B. However, numerous adverse effects have been reported for echinocandin antifungal agents including headache, fever, liver toxic effects, phlebitis, histamine release, haemolysis and rash. See, for example, Denning, "Echinocandin antifungal drugs," Lancet 2003; 362: 1142-51.

Accordingly, a need exists for new methods of administering echinocandin antifungal agents that reduce the side effects of such agents. In particular, a need exists for new methods and compositions that enhance the efficacy of such antifungal agents thereby permitting such agents to be administered in reduced amounts.

SUMMARY OF THE INVENTION

The present invention provides a novel method of administering an echinocandin antifungal agent in combination with a glycopeptide antibacterial agent. Surprisingly, it has now been discovered that, when a glycopeptide antibacterial agent having a substituent comprising at least about 8 carbon atoms is administered in combination with an echinocandin antifungal agent, the efficacy of the echinocandin antifungal agent is substantially increased. Accordingly, when used in combination with such a glycopeptide antibacterial agent, the amount of echinocandin antifungal agent needed to treat a fungal infection is reduced.

Accordingly, in one of its method aspects, this invention provides a method for administering an echinocandin antifungal agent to a subject, the method comprising administering to the subject an echinocandin antifungal agent and a glycopeptide antibacterial agent having a substituent comprising at least about 8 carbon atoms.

In another of its method aspects, this invention provides a method for treating a fungal infection in a subject, the method comprising administering to the subject an antifungal amount of an echinocandin antifungal agent and a glycopeptide antibacterial agent having a substituent comprising at least about 8 carbon atoms.

In yet another of its method aspects, this invention provides a method for increasing the efficacy of an echinocandin antifungal agent, the method comprising administering the echinocandin antifungal agent to a subject in combination with a glycopeptide antibacterial agent having a substituent comprising at least about 8 carbon atoms.

In one of its composition aspects, this invention provides a pharmaceutical composition comprising:
 (a) an echinocandin antifungal agent;
 (b) a glycopeptide antibacterial agent having a substituent comprising at least about 8 carbon atoms; and
 (c) a pharmaceutically acceptable carrier.

In another aspect, this invention provides a kit comprising:
 (a) an echinocandin antifungal agent; and
 (b) a glycopeptide antibacterial agent having a substituent comprising at least about 8 carbon atoms.

In one embodiment, the kit further comprises instructions for administering the antifungal and antibacterial agents to a subject in need of treatment.

In yet another aspect, this invention provides a system for treating a fungal infection in a subject, the system comprising:
 (a) an echinocandin antifungal agent; and
 (b) a glycopeptide antibacterial agent having a substituent comprising at least about 8 carbon atoms.

This invention is also directed to the use of:
 (a) an echinocandin antifungal agent; and
 (b) a glycopeptide antibacterial agent having a substituent comprising at least about 8 carbon atoms;
in the manufacture of a medicament for the treatment of a fungal infection.

In particular, this invention is directed to the use of an echinocandin antifungal agent in the manufacture of a medicament for administration in combination with a glycopeptide antibacterial agent having a substituent comprising at least about 8 carbon atoms for the treatment of a fungal infection.

Moreover, this invention is directed to the use of a glycopeptide antibacterial agent having a substituent comprising at least about 8 carbon atoms in the manufacture of a medicament for administration in combination with an echinocandin antifungal agent for the treatment of a fungal infection.

In yet another of its aspects, this invention provides a combination comprising:
 (a) an echinocandin antifungal agent; and
 (b) a glycopeptide antibacterial agent having a substituent comprising at least about 8 carbon atoms.

DETAILED DESCRIPTION OF THE INVENTION

The present invention provides a novel method of administering an echinocandin antifungal agent to a subject in need of treatment. A feature of the present invention is that the echinocandin antifungal agent is administered to the subject in combination with a glycopeptide antibacterial agent having a substituent comprising at least about 8 carbon atoms. The antifungal and antibacterial agents may be administered sequentially or simultaneously; and may be in the same or separate formulations. Also provided are compositions, including pharmaceutical compositions, kits and systems, comprising an echinocandin antifungal agent and a glycopeptide antibacterial agent as defined herein.

Before the present invention is described further, it is to be understood that the invention is not limited to the particular embodiments of the invention described herein, as variations of the particular embodiments may be made and still fall within the scope of the appended claims. It is also to be understood that the terminology employed herein is for the purpose of describing particular embodiments and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood by one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Definitions

When describing the compounds, compositions, methods, kits, systems and processes of this invention, the following terms have the following meanings unless otherwise indicated.

The term "alkyl" means a monovalent saturated hydrocarbon group which may be linear or branched. Unless otherwise defined, such alkyl groups typically contain from 1 to 15 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

When a specific number of carbon atoms is intended for a particular term used herein, the number of carbon atoms is shown preceding the term. For example, the term "$C_{8\text{-}12}$ alkyl" means an alkyl group having from 8 to 12 carbon atoms.

The term "alkylene" means a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkenyl" means a monovalent unsaturated hydrocarbon group which may be linear or branched and which has at least one, and typically 1, 2 or 3, carbon-carbon double bonds. Unless otherwise defined, such alkenyl groups typically contain from 2 to 15 carbon atoms. Representative alkenyl groups include, by way of example, ethenyl, n-propenyl, isopropenyl, n-but-2-enyl, n-hex-3-enyl and the like.

The term "alkynyl" means a monovalent unsaturated hydrocarbon group which may be linear or branched and which has at least one, and typically 1, 2 or 3, carbon-carbon triple bonds. Unless otherwise defined, such alkynyl groups typically contain from 2 to 15 carbon atoms. Representative alkynyl groups include, by way of example, ethynyl, n-propynyl, n-but-2-ynyl, n-hex-3-ynyl and the like.

The term "alkoxy" means a monovalent group of the formula (alkyl)-O—, where alkyl is as defined herein. Representative alkoxy groups include, by way of example, methoxy, ethoxy, n-propoxy, isopropoxy, n-butoxy, sec-butoxy, isobutoxy, tert-butoxy and the like.

The term "thioalkoxy" means a monovalent group of the formula (alkyl)-S—, where alkyl is as defined herein. Representative thioalkoxy groups include, by way of example, $CH_3$—S—, $CH_3CH_2$—S—, $CH_3CH_2CH_2$—S—, $(CH_3)_2CH_2$—S—, and the like.

The term "halo" means fluoro, chloro, bromo and iodo.

The term "heteroaryl" means a monovalent aromatic group having a single ring or two fused rings and containing in the ring at least one heteroatom (typically 1 to 3 heteroatoms) selected from nitrogen, oxygen or sulfur. Unless otherwise defined, such heteroaryl groups typically contain from 5 to 10 total ring atoms. Representative heteroaryl groups include, by way of example, monovalent species of pyrrole, imidazole, thiazole, oxazole, oxadiazole, furan, thiophene, triazole, pyrazole, isoxazole, isothiazole, thiadiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom. Representative heteroaryls include isoxazolyl, thiadiazolyl, oxadiazolyl, imidazolyl, pyridyl, pyrrolyl and furyl.

The term "heteroarylene" means a divalent heteroaryl group.

The term "saccharide group" means an oxidized, reduced or substituted saccharide monoradical covalently attached to the glycopeptide or other compound via any atom of the saccharide moiety, e.g., via the aglycone carbon atom. The term includes amino-containing saccharide groups. Representative saccharide include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. For the purposes of this definition, the saccharide can be either in its open or in cyclic form (i.e., the pyranose form for hexoses).

The term "amino-containing saccharide group" means a saccharide group having an amino substituent. Representative amino-containing saccharides include L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like.

A "substituent comprising at least 8 carbon atoms" means any substituent having at least 8 carbon atoms which substituent may also contain other atoms such as oxygen, nitrogen, sulfur or halo; or combinations thereof. When attached to a glycopeptide antibacterial agent, such a substituent is attached to either (1) the amino acids (AA 1-7) that form the core of the glycopeptide antibacterial agent, or (2) a mono- or polysaccharide group of the glycopeptide antibacterial agent. When determining the number of carbon atoms in the substituent, this term does not include any carbon atoms of the amino acids (AA 1-7) that form the core of the glycopeptide, or any carbon atoms that form the rings of a mono- or polysaccharide group attached to the glycopeptide core.

"Pharmaceutically acceptable salt" means those salts which retain the biological effectiveness and properties of the parent compounds and which are not biologically or otherwise harmful at the dosage administered. Active agents employed in methods of the subject invention are capable of forming both acid and base salts by virtue of the presence of amino and carboxy groups respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The term "treating" or "treatment" as used herein means the treating or treatment of a disease or medical condition (such as a fungal infection) in a subject or patient, such as a mammal (particularly a human) that includes:

(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

The term "therapeutically effective amount" means an amount sufficient to effect treatment when administered to a subject or patient in need of treatment. The therapeutically effective amount will vary depending on the subject and disease state being treated, the severity of the affliction and the manner of administration, and may be determined routinely by one of ordinary skill in the art.

The term "antifungal amount" means an amount sufficient to treat a fungal infection or medical condition.

The term "antibacterial amount" means an amount sufficient to treat a bacterial infection or medical condition.

The Glycopeptide Antibacterial Agent

The glycopeptide antibacterial agent employed in this invention is any glycopeptide antibacterial agent having a substituent comprising at least about 8 carbon atoms. Glycopeptide antibacterial agents are a well known class of antibacterial agents. See, for example, Nicolaou et al., *Angew. Chem. Int. Ed.* (1999) 38:2096-2152; and Rao et al., Glycopeptides Classification, Occurrence, and Discovery. In *Glycopeptide Antibiotics*; Ramakrishnan Nagarajan Ed.; Marcel Dekker, Inc.: New York, N.Y., 1994; Volume 63, pp 1-27.

Glycopeptide antibacterial agents typically have a multi-ring peptide core comprising seven amino acids (i.e., AA-1 to AA-7) and at least 5 aromatic rings (i.e., rings A through E). The peptide core is optionally substituted with one or more saccharide groups. Type I structures contain aliphatic rings in AA-1 and AA-3. Type II, type III and type IV structures include aromatic side chains within these amino acids. Furthermore, type III and IV structures contain an extra F-O-G ring system. In addition, type IV compounds have a long fatty-acid chain attached to the sugar moiety. Type V compounds contain a tryptophan moiety linked to the central amino acid.

Examples of glycopeptide antibacterial agents include those identified as A477, A35512, A40926, A41030, A42867, A47934, A80407, A82846, A83850, A84575, AB-65, actaplanin, actinoidin, ardacin, avoparcin, azureomycin, balhimycin, chloroorientiein, chloropolysporin, dalbavancin, decaplanin, N-demethylvancomycin, eremomycin, galacardin, helvecardin, izupeptin, kibdelin, LL-AM374, mannopeptin, MM45289, MM47756, MM47761, MM49721, MM47766, MM55260, MM55266, MM55270, MM56597, MM56598, OA-7653, orenticin, oritivancin, parvodicin, ristocetin, ristomycin, synmonicin, teicoplanin, telavancin, UK-68597, UK-69542, UK-72051, vancomycin, and the like; and semi-synthetic derivatives thereof.

Additional examples of glycopeptide antibacterial agents are disclosed in U.S. Pat. Nos. 4,639,433; 4,643,987; 4,497,802; 4,698,327; 5,591,714; 5,840,684; and 5,843,889; in EP 0 802 199; EP 0 801 075; EP 0 667 353; WO 97/28812; WO 97/38702; WO 98/52589; WO 98/52592; and in *J. Amer. Chem. Soc.*, 1996, 118, 13107-13108; *J. Amer. Chem. Soc.*, 1997, 119, 12041-12047; and *J. Amer. Chem. Soc.*, 1994, 116, 4573-4590.

Another group of glycopeptide antibacterial agents are those in which the N-terminal amino acid of a naturally-occurring glycopeptide antibacterial agent has been removed (i.e., a hexapeptide). Methods for preparing such hexapeptides are disclosed in U.S. Pat. No. 5,952,310; and P. M. Booth et al., *J. Chem. Soc., Chem. Commun.* (1987) 1964-1965.

The term "semi-synthetic glycopeptide antibacterial agent" means a glycopeptide antibacterial agent that is produced by modifying a naturally-occurring glycopeptide antibacterial agent, e.g., through modification of the outer sphere of the parent compound; or through degradation and reassembly of the cyclopeptide core with incorporation, for example, of new amino acid components. The term "synthetic glycopeptide antibacterial agent" means any non-naturally occurring glycopeptide antibacterial agent, whether or not it is a modified naturally-occurring compound, i.e., a semi-synthetic compound. When defining the glycopeptide antibacterial agents of this invention, the terms "type I," "type II," "type III," "type IV," "type V," "semi-synthetic," and "outer-sphere" are used as defined in the art (for example, as used the above cited Nicolaou et al., review).

The particular glycopeptide antibacterial agents used in this invention are those having a substituent comprising at least about 8 carbon atoms. In this regard, the glycopeptide antibacterial agent may be a naturally-occurring glycopeptide antibacterial agent or a synthetic glycopeptide antibacterial agent (including a semi-synthetic glycopeptide antibacterial agent).

Typically, the substituent comprising at least about 8 carbon atoms will contain from about 8 to about 24 carbon atoms, including from about 8 to about 20 carbon atoms, such as from about 8 to about 14 carbon atoms; and from 0 to about 5 heteroatoms selected from oxygen, nitrogen, sulfur or halo. The carbon atoms of such substituents may be linear or branched or may be joined to form aliphatic or aromatic rings, such as phenyl rings. The optional heteroatoms may interrupt the carbon chain, i.e., to form ethers, thioethers or amines, or may be substituents attached to the carbon chain, such as a chloro substituent.

In certain embodiments, the glycopeptide antibacterial agent is a compound of formula I:

wherein $X^1$ and $X^2$ are independently hydrogen or chloro;

$R^1$ selected from the group consisting of:

(a) —$R^a$;
(b) —C(O)—$R^b$;
(c) —$R^c$—$W^1$;
(d) —C(O)—$R^d$—$W^2$; and
(e) —$R^e$—Y—$R^f$;

where $R^a$ and $R^b$ are independently $C_{8-14}$ alkyl, $C_{8-14}$ alkenyl or $C_{8-14}$ alkynyl;

$R^c$ and $R^d$ are independently $C_{1-8}$ alkylene;

$R^e$ is $C_{2-8}$ alkylene;

$R^f$ is $C_{1-12}$ alkyl, $C_{2-12}$ alkenyl or $C_{2-12}$ alkynyl;

$W^1$ and $W^2$ are independently phenyl optionally substituted with 1 to 3 substituents independently selected from the group consisting of $C_{1-6}$ alkyl, $C_{1-6}$ alkoxy, halo, -(phenyl), —CH$_2$-(phenyl), —O-(phenyl), and —O—CH$_2$-(phenyl); wherein each -(phenyl) group is optionally substituted with 1 or 2 substituents independently selected from the group consisting of $C_{1-6}$ alkyl, $C_{1-6}$ alkoxy and halo;

Y is O, S or NH;

and provided that $R^1$ comprises at least 8 carbon atoms;

one of $R^2$ and $R^3$ hydroxy and the other is hydrogen;

$R^4$ and $R^5$ are independently hydrogen or methyl;

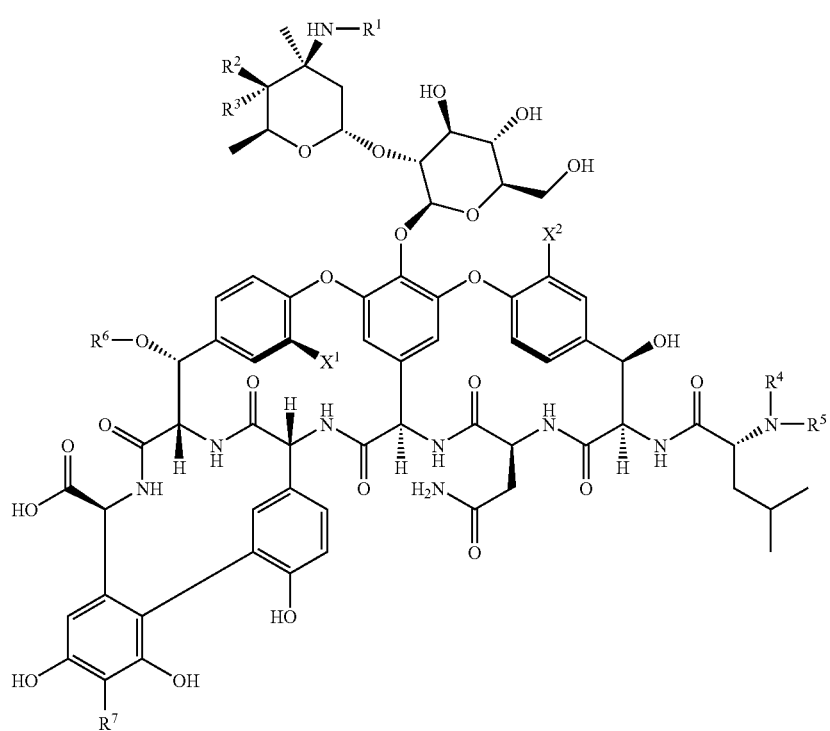

I $R^6$ is hydrogen or a group of formula (f):

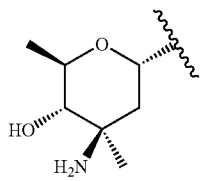

(f)

$R^7$ is hydrogen or a group of formula (g):

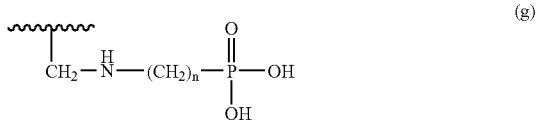

(g)

n is an integer from 1 to 6;
or a pharmaceutically-acceptable salt thereof or stereoisomer thereof.

In a specific embodiment of interest, the glycopeptide antibacterial agent is a compound of formula I, where: $X^1$ and $X^2$ are both chloro; $R^1$ is —$CH_2CH_2$—NH—$(CH_2)_9CH_3$; $R^2$ is hydroxy; $R^3$ is hydrogen; $R^4$ is methyl; $R^5$ is hydrogen; $R^6$ is hydrogen; and $R^7$ is —$CH_2$—NH—$CH_2$—$P(O)(OH)_2$. This compound is known in the art as telavancin.

In another specific embodiment of interest, the glycopeptide antibacterial agent is a compound of formula I, where: $X^1$ and $X^2$ are both chloro; $R^1$ is a group of the formula:

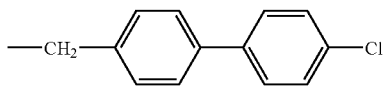

$R^2$ is hydrogen; $R^3$ is hydroxy; $R^4$ is methyl; $R^5$ is hydrogen; $R^6$ is a group of formula (f); and $R^7$ is hydrogen. This compound is known in the art as oritavancin.

In another specific embodiment of interest, the glycopeptide antibacterial agent is a compound of formula I, where: $X^1$ and $X^2$ are both chloro; $R^1$ is a group of the formula:

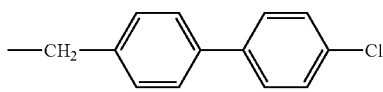

$R^2$ is hydroxy; $R^3$ is H; $R^4$ is methyl; $R^5$ is hydrogen; $R^6$ is hydrogen; and $R^7$ is hydrogen.

In yet another specific embodiment of interest, the glycopeptide antibacterial agent is dalbavancin.

In yet another specific embodiment of interest, the glycopeptide antibacterial agent is a teicoplanin. As used herein, the term teicoplanin include teicoplanin $A_2$-1 to 5, i.e., includes one or more of teicoplanin $A_2$-1; teicoplanin $A_2$-2; teicoplanin $A_2$-3; teicoplanin $A_2$-4; and teicoplanin $A_2$-5.

In a particular embodiment, the glycopeptide antibacterial agent is selected from telavancin, oritavancin, dalbavancin and teicoplanin; or a pharmaceutically acceptable salt thereof.

Also of interest are derivatives of such compounds, e.g., compounds in which modifications to one or more of the above moieties or groups have been made and which derivatives retain antibacterial activity.

Such glycopeptide antibacterial agents are commercially available or can be conventionally prepared by techniques known to one of skill in the art. For example, representative patents describing various glycopeptide compounds and derivatives thereof, as well as the synthesis or preparation thereof, include U.S. Pat. Nos. 4,497,802; 4,639,433; 4,643,987; 4,698,327; 5,591,714; 5,750,509; 5,916,873; 5,919,756; 5,840,684; 5,840,684; 5,843,889; 5,977,062; and 6,444,786; as well as published U.S. Application Publication Nos. 2002/0022590 A1; 2003/008812 A1; 2003/0045457 A1; and 2003/0069391 A1.

The Echinocandin Antifungal Agent

The echinocandin antifungal agents employed in this invention are a well known class of antifungal agents. See, for example, Denning, "Echinocandin antifungal drugs," *Lancet* 2003; 362: 1142-51. Such echinocandin antifungal agents include lipopeptide agents which are cyclopeptides, e.g., cyclic hexapeptides, as well as non-cyclopeptide functional analogues thereof, e.g., corynecandin, etc.

The echinocandin antifungal agent employed in this invention may be a naturally-occurring echinocandin antifungal agent or a synthetic or semi-synthetic derivative thereof.

Representative naturally-occurring echinocandin antifungal agents of interest include, but are not limited to: echinocandin B (ECB), echinocandin C, aculeacin Aγ, mulundocandin, sporiofungin A, pneumocandin $A_0$, WF11899A, and pneumocandin $B_0$.

Synthetic and semi-synthetic echinocandin antifungal agents of interest include analogues of the above naturally-occurring echinocandin compounds, e.g., analogues of echinocandin B, such as cilofungin and anidulafungin; analogues of WF11899A, such as micafungin; and analogues of pneumocandin Bo, such as caspofungin.

The echinocandin antifungal agents employed in this invention are commercially available or can be prepared by techniques known to those skilled in the art. For example, representative patents and patent applications describing various echinocandin antifungal agents and derivatives thereof, as well as the synthesis and preparation of such agents, include U.S. Pat. Nos. 5,378,804; 5,514,650; 5,541,160; 5,782,746; 5,952,300; 6,136,783; 6,107,458; 6,232,290; US 2003/0017975; WO 98/52967; WO 99/20651; WO 99/29716; WO 99/43337; WO 99/55727; WO 00/11023; WO 00/34315; WO 00/51564; WO 00/51567; WO 00/52036; WO 00/52037; WO 00/63239; WO 00/75177; WO 00/75178; WO 01/02002; and WO 01/07468.

In one embodiment, the echinocandin antifungal agent is a compound of formula II:

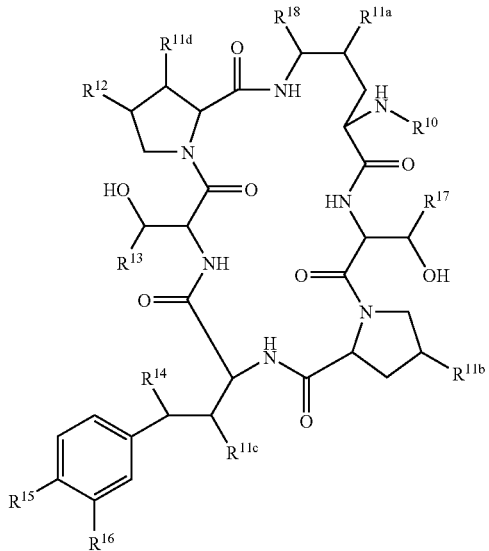

wherein:
$R^{10}$ is selected from the group consisting of:
(a) hydrogen;
(b) —C(O)$R^g$;
(C) —C(O)—$W^3$—$R^h$;
(d) —C(O)—$W^3$—$W^3$—$R^h$;
(e) —C(O)—$W^3$—$W^4$—$W^3$—$R^h$;
(f) —C(O)—$W^3$—C≡C—$W^3$—$R^h$;
(g) —C(O)—$W^3$—$W^3$—C≡C—$W^3$—$R^h$;

where
$R^g$ is $C_{1-20}$ alkyl, $C_{2-20}$ alkenyl or $C_{2-20}$ alkynyl;
$R^h$ is selected from the group consisting of hydrogen, $C_{1-12}$ alkyl, $C_{2-12}$ alkenyl, $C_{2-12}$ alkynyl, $C_{1-12}$ alkoxy, $C_{1-12}$ thioalkoxy, halo and —O—(CH$_2$)$_p$—O—$C_{1-12}$ alkyl, where p is 2 to 12;
each $W^3$ and $W^4$ is independently 1,4-phenylene or $C_{3-6}$ heteroarylene containing 1 to 3 heteroatoms selected from the group consisting of oxygen, nitrogen or sulfur; wherein the phenylene or heteroarylene group is optionally substituted with 1 to 3 substituents independently selected from the group consisting of $C_{1-6}$ alkyl, $C_{2-6}$ alkenyl, $C_{2-6}$ alkynyl, $C_{1-6}$ alkoxy, $C_{1-6}$ thioalkoxy and halo;
$R^{11a}$, $R^{11b}$, $R^{11c}$, and $R^{11d}$ are independently selected from hydrogen or hydroxy; or $R^{11a}$ is —NH(CH$_2$)$_2$NH$_2$ or —NH-(2-aminocyclohex-1-yl);
$R^{12}$ is hydrogen, hydroxy, amino or methyl;
$R^{13}$ is hydrogen, methyl, —CH$_2$CN, —CH$_2$CONH$_2$ or —CH$_2$CH$_2$NH$_2$;
$R^{14}$ is hydrogen or hydroxy;
$R^{15}$ is hydroxy, —OP(O)(OH)$_2$, —OP(O)(OH)(OCH$_3$), —OP(OH)(OCH$_3$) or —OSO$_3$H;
$R^{16}$ is hydrogen, hydroxy, —OSO$_3$H, —SO$_3$H or —CH$_2$-piperidin-1-yl;
$R^{17}$ is hydrogen or methyl; and
$R^{18}$ is hydrogen, hydroxy, benzyloxy, —NR$^i$R$^j$ or —O—(CH$_2$)$_{2-6}$NR$^k$R$^l$, where R$^i$ is hydrogen, $C_{1-4}$ alkyl, $C_{3-4}$ alkenyl, —(CH$_2$)$_{2-4}$OH, —(CH$_2$)$_{2-4}$NR$^k$R$^l$ or —CO(CH$_2$)$_{1-4}$NH$_2$; where R$^j$ is hydrogen, $C_{1-4}$ alkyl, $C_{3-4}$ alkenyl, —(CH$_2$)$_{2-4}$OH or —(CH$_2$)$_{2-4}$NR$^k$R$^l$; or R$^i$ and R$^j$ taken together are —(CH$_2$)$_4$—, —(CH$_2$)$_5$—, —(CH$_2$)$_2$O(CH$_2$)$_2$— or —(CH$_2$)$_2$—NH—(CH$_2$)$_2$—; and where each R$^k$ and R$^l$ are independently hydrogen or $C_{1-4}$ alkyl;
or a pharmaceutically acceptable salt or stereoisomer thereof.

In one embodiment of formula II, $R^{10}$ is —C(O)$R^g$, where $R^g$ is as defined herein. In a specific embodiment of this aspect of the invention, $R^g$ is selected from the group consisting of $C_{1-20}$ alkyl and $C_{2-20}$ alkenyl. Examples of particular values for $R^g$ are —(CH$_2$)$_{14}$—CH$_3$, —(CH$_2$)$_8$—[CH(CH$_3$)—CH$_2$—]$_2$—CH$_3$, —(CH$_2$)$_{10}$—CH(CH$_3$)—CH$_2$—CH$_3$, —(CH$_2$)$_7$—CH=CH—CH$_2$—CH=CH—(CH$_2$)$_4$—CH$_3$ and —[CH=C(CH$_3$)—(CH$_2$)$_2$—]$_2$—CH=C(CH$_3$)$_2$.

In another embodiment of formula II, $R^{10}$ is —C(O)—$W^3$—$R^h$, where $W^3$ and $R^h$ are as defined herein. In a specific embodiment of this aspect of the invention, $W^3$ is unsubstituted 1,4-phenylene; and $R^h$ is selected from the group consisting of $C_{1-12}$ alkoxy and —O—(CH$_2$)$_p$—O—$C_{1-12}$ alkyl, where p is 2 to 12. Particular values of $R^h$ for this and other embodiments are —O(CH$_2$)$_4$CH$_3$, —O(CH$_2$)$_5$CH$_3$, —O(CH$_2$)$_6$CH$_3$, —O(CH$_2$)$_7$CH$_3$, —O(CH$_2$)$_8$CH$_3$, —O—(CH$_2$)$_6$—O—CH$_3$ and —O—(CH$_2$)$_2$—O—(CH$_2$)$_7$—CH$_3$.

Examples of particular values for —$W^3$—$R^h$ are:

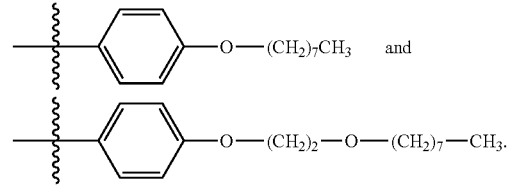

In still another embodiment of formula II, $R^{10}$ is —C(O)—$W^3$—$W^3$—$R^h$, where each $W^3$ and $R^h$ are as defined herein. In a specific embodiment of this aspect of the invention, each $W^3$ is unsubstituted 1,4-phenylene; and $R^h$ is selected from the group consisting of $C_{1-12}$ alkoxy and —O—(CH$_2$)$_p$—O—$C_{1-12}$ alkyl, where p is 2 to 12.

An example of a particular value for —$W^3$—$W^3$—$R^h$ is:

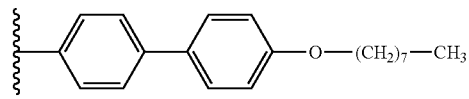

In yet another embodiment of formula II, $R^{10}$ is C(O)—$W^3$—$W^4$—$W^3$—$R^h$, where each $W^3$, $W^4$ and $R^h$ are as defined herein. In a specific embodiment of this aspect of the invention, each $W^3$ is unsubstituted 1,4-phenylene; $W^4$ is unsubstituted 1,4-phenylene or unsubstituted heteroarylene selected from the group consisting of 1,3,4-thiadiazol-2,5-diyl, isoxazol-3,5-diyl, 1,3,4-oxadiazol-2,5-diyl, 1,2,4-oxadiazol-3,5-diyl and imidazol-2,4-diyl; and $R^h$ is selected from the group consisting of $C_{1-12}$ alkoxy and —O—(CH$_2$)$_p$—O—$C_{1-12}$ alkyl, where p is 2 to 12.

Examples of particular values for —$W^3$—$W^4$—$W^3$—$R^h$ are:

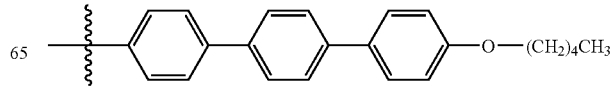

-continued

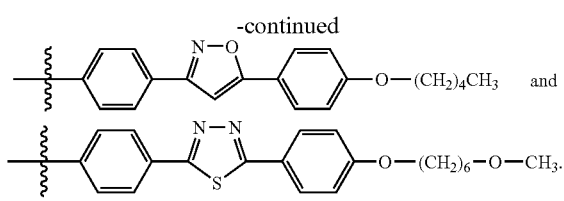

In a specific embodiment of formula II, $R^{10}$ is selected from the group consisting of:

hydrogen;

—C(O)—(CH$_2$)$_{14}$—CH$_3$;

—C(O)—(CH$_2$)$_8$—[CH(CH$_3$)—CH$_2$—]$_2$—CH$_3$;

—C(O)—(CH$_2$)$_7$—CH═CH—CH$_2$—CH═CH—(CH$_2$)$_4$—CH$_3$;

—C(O)-[CH═C(CH$_3$)—(CH$_2$)$_2$—]$_2$—CH═C(CH$_3$)$_2$;

—C(O)—(CH$_2$)$_{10}$—CH(CH$_3$)—CH$_2$—CH$_3$;

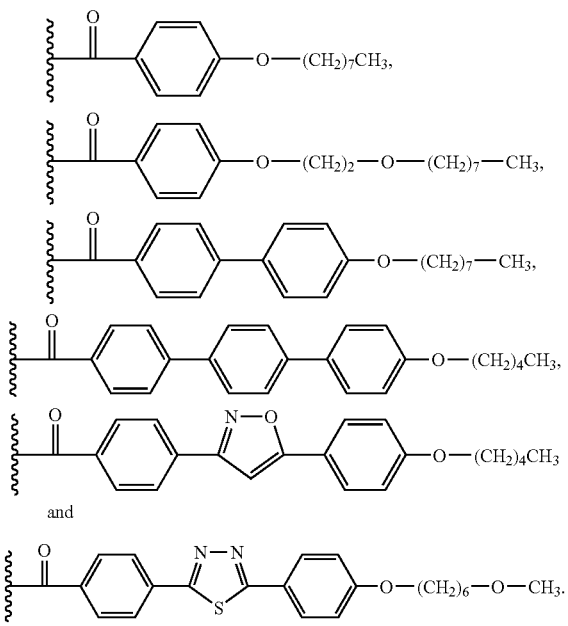

and

Particular values of $R^{10}$ can be selected from the group consisting of

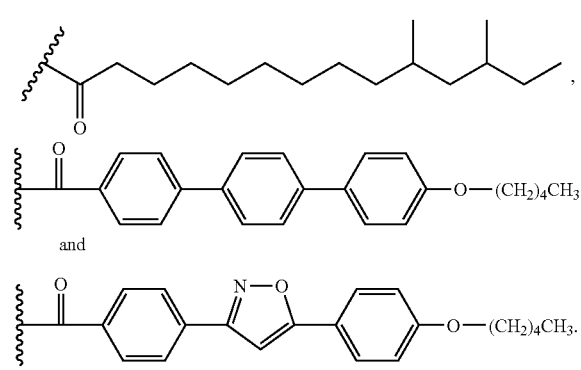

In a specific embodiment of interest, the echinocandin antifungal agent employed in this invention is a compound of formula II, where $R^{10}$ is a group of the formula:

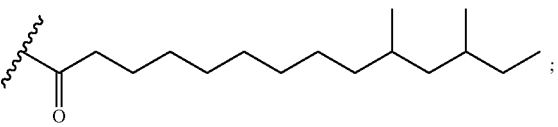

$R^{11a}$, $R^{11b}$, $R^{11c}$, and $R^{11d}$ are —OH; $R^{12}$ is —H; $R^{13}$—(CH$_2$)$_2$—NH$_2$; $R^{14}$ is —OH; $R^{15}$ is —OH; $R^{16}$ is —H; $R^{17}$ is —CH$_3$; and $R^{18}$ is —NH—(CH$_2$)$_2$—NH$_2$. This compound is known as caspofungin.

In another specific embodiment of interest, the echinocandin antifungal agent is a compound of formula II, where $R^{10}$ is a group of the formula:

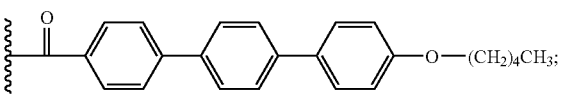

$R^{11a}$, $R^{11b}$, $R^{11c}$, and $R^{11d}$ are —OH; $R^{12}$ and $R^{13}$ are —CH$_3$; $R^{14}$ and $R^{15}$ are —OH; $R^{16}$ is —H; $R^{17}$ is —CH$_3$; and $R^{18}$ is —OH. This compound is known as anidulafungin.

In another specific embodiment of interest, the echinocandin antifungal agent is a compound of formula II, where $R^{10}$ is a group of the formula:

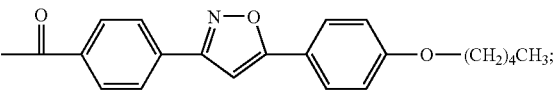

$R^{11a}$, $R^{11b}$, $R^{11c}$, and $R^{11d}$ are —OH; $R^{12}$ is —CH$_3$; $R^{13}$ is —CH$_2$—C(O)—NH$_2$; $R^{14}$ and $R^{15}$ are —OH; $R^{16}$ is —SO$_3$H; $R^{17}$ is —CH$_3$; and $R^{18}$ is —OH. This compound is known as micafungin.

In one embodiment, the echinocandin antifungal agent is selected from the group consisting of caspofungin, anidulafungin and micafungin. In a particular embodiment, the echinocandin agent is caspofungin. In one embodiment, the glycopeptide antibacterial agent is telavancin and the echinocandin antifungal agent is caspofungin.

Methods

The present invention provides methods of administering an echinocandin antifungal agent to a subject in need of treatment. A feature of the present methods is that the echinocandin antifungal agent is administered to the subject in combination with a glycopeptide antibacterial agent having a substituent comprising at least about 8 carbon atoms.

By "in combination with" is meant that an amount of an echinocandin antifungal agent is administered to the subject together with an amount of a glycopeptide antibacterial agent. In certain embodiments, the echinocandin antifungal agent and glycopeptide antibacterial agent are administered sequentially, e.g., where the echinocandin antifungal agent is administered before or after the glycopeptide antibacterial agent. In other embodiments, the echinocandin antifungal agent and glycopeptide antibacterial agent are administered simultaneously, e.g., where the echinocandin antifungal agent and glycopeptide antibacterial agent are administered at the same time as two separate formulations or are combined into a single composition that is administered to the subject. Regardless of whether the echinocandin antifungal agent and glycopeptide antibacterial agent are administered sequentially or simultaneously, the agents are considered to be administered together or in combination for purposes of the present invention if both agents are present in the patient at the same time.

Routes of administration of the two agents and the amount of each agent employed will depend on various factors, such as the particular agents being used, the condition being treated and so forth. Generally, the amount of the echinocandin antifungal agent that is administered to the subject is a therapeutically effective amount to treat the subject for the condition afflicting the subject, e.g., for the fungal infection afflicting the subject. In many embodiments, this effective amount is one that is less than the amount which is effective when the echinocandin antifungal agent is not administered in combination with a glycopeptide antibacterial agent (i.e., in a control administration). For example, when administered according to this invention, the amount of echinocandin antifungal agent can typically be reduced by at least about 10% by weight per dose; in other cases, by at least about 20% by weight per dose; and in still other cases, by at least about 50% by weight per dose. In certain representative embodiments, such as when administered by IV infusion, the amount of echinocandin antifungal agent that is administered to the subject ranges from about 25 mg per day to about 100 mg per day, such as from about 50 mg per day to about 70 mg per day.

The amount of glycopeptide antibacterial agent that is administered to the subject is one that typically increases the efficacy of the echinocandin antifungal agent, where efficacy is considered to be increased if the amount of the echinocandin antifungal agent required to be effective is decreased by at least about 10% by weight per dose. In certain embodiments, the amount of glycopeptide agent administered to the subject is one that results in a synergistic increase in the efficacy of the echinocandin antifungal agent. By synergistic increase is meant that the amount of glycopeptide antibacterial agent administered to the subject causes the efficacy of the co-administered echinocandin antifungal agent to increase synergistically. Synergy can be demonstrated in vitro using, for example, the checkerboard MIC assay, as described in Eliopoulos, E. G. and R. Moellering, Jr. "Antimicrobial Combinations" in *Antibiotics in Laboratory Medicine*, edited by V. Lorian, 4$^{th}$ Ed., Williams & Wilkins, Baltimore, Md., pp. 330-396 (1996); Shalit et al., Antimicrobial Agents and Chemotherapy 47(4):1416-1418 (2003); or Afeltra et al., Antimicrobial Agents and Chemotherapy 46(10):3323-3326 (2002); and as illustrated in the Experimental Section herein. In many embodiments, the amount of glycopeptide antibacterial agent that is administered is sufficient to result in a Functional Inhibitory Concentration Index (FICI) of $\leq 0.7$, including $\leq 0.6$, such as $\leq 0.5$, as determined using the MIC assay.

In certain embodiments, for example, when administered by IV infusion, the amount of glycopeptide antibacterial agent that is administered to the subject in any given dose ranges from about 0.1 mg/kg to about 50 mg/kg, such as from about 0.25 mg/kg to about 25 mg/kg, including from about 0.5 mg/kg to about 10 mg/kg.

In practicing the methods of this invention, the combination of an echinocandin antifungal agent and a glycopeptide antibacterial agent can be administered in a single daily dose or in multiple doses per day. The treatment regimen may require administration over extended periods of time, for example, for several days or for from one to six weeks.

Pharmaceutical Compositions

The echinocandin antifungal agent and the glycopeptide antibacterial agent employed in this invention are typically formulated as a pharmaceutical composition suitable for administration to a subject in need of treatment. In this regard, the echinocandin antifungal agent and the glycopeptide antibacterial agent may be formulated as separate pharmaceutical compositions for administration simultaneously or sequentially to a subject in need of treatment. Alternatively, such agents may be combined in a single pharmaceutical composition, i.e., one composition that includes both active agents.

Generally, when formulated and administered as separate pharmaceutical compositions, the echinocandin antifungal agent and the glycopeptide antibacterial agent will be formulated using conventional pharmaceutical compositions well known and previous described in the art for such agents.

For example, pharmaceutical compositions suitable for echinocandin antifungal agents are described in U.S. Pat. Nos. 5,378,804; 5,952,300; and 6,136,783; and WO00/51564; WO00/51567; WO99/43337; and WO98/52967. Suitable caspofungin formulations include, for example, Cancidas®.

Additionally, pharmaceutical compositions suitable for glycopeptide antibacterial agents are described in U.S. Pat. Nos. 5,977,062 and 6,635,618; EP 0 667 353; EP 0 525 499; and WO01/82971.

When the echinocandin antifungal agent and the glycopeptide antibacterial agent are formulated together in a single pharmaceutical composition, such compositions are novel. Accordingly, in one embodiment, this invention is directed to a pharmaceutical composition comprising an echinocandin antifungal agent; a glycopeptide antibacterial agent having a substituent comprising at least about 8 carbon atoms; and a pharmaceutically acceptable carrier, excipient or vehicle.

By way of further illustration, the echinocandin antifungal agent and/or the glycopeptide antibacterial agent can be admixed with conventional pharmaceutical carriers and excipients (i.e., vehicles) and used in the form of aqueous solutions, tablets, capsules, elixirs, suspensions, syrups, wafers, and the like. Such pharmaceutical compositions generally contain, in certain embodiments, from about 0.1 to about 90% by weight of the active compound, and more generally from about 1 to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent.

Alternatively, a liquid formulation can be prepared from a reconstitutable powder. For example, a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the invention and their pharmaceutically acceptable salts that are active when given parenterally can be formulated for intramuscular, intrathecal, or intravenous administration.

A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetraacetic acid, and an anti-oxidant, for example, sodium metabisulphite may be included in the formulation. Alternatively, the solution can be freeze dried and then reconstituted with a suitable solvent just prior to administration.

The compounds of the invention and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds of this invention and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present invention in controlled amounts. The construction and use of transdermal patches for the delivery of pharmaceutical agents is well known in the art. See, for example, U.S. Pat. No. 5,023,252, issued Jun. 11, 1991. Such patches may be constructed for continuous, pulsatile, or on demand delivery of pharmaceutical agents.

In certain embodiments, the pharmaceutical composition containing the glycopeptide antibacterial agent will further comprise a cyclodextrin compound. By way of illustration, the glycopeptide antibacterial agent, for example, in the form a pharmaceutically acceptable salt, can be admixed with an aqueous cyclodextrin solution to form a pharmaceutical composition. Such pharmaceutical compositions will typically contain from about 1 to about 40 weight per ent of the cyclodextrin and an effective amount of the glycopeptide antibacterial agent. In certain embodiments, the cyclodextrin employed in the pharmaceutical compositions of this invention is hydroxypropyl-β-cyclodextrin or sulfobutyl ether β-cyclodextrin. In certain embodiments, the cyclodextrin is hydroxypropyl-β-cyclodextrin. In certain embodiments, the cyclodextrin will comprise about 1 to 40 weight percent; such as about 2 to 30 weight percent; including about 5 to 15 weight percent, of the formulation. In an embodiment, the aqueous cyclodextrin solution further comprises dextrose, e.g., about 5% dextrose.

Optionally, the pharmaceutical composition may contain other pharmaceutically acceptable components, such a buffers, surfactants, antioxidants, viscosity modifying agents, preservatives and the like. Each of these components is well known in the art. See, for example, U.S. Pat. No. 5,985,310.

Other components suitable for use in the formulations of the present invention can be found in *Remington: The Science and Practice of Pharmacy*, 20th Edition, Lippinoft Williams & White, Baltimore, Md. (2000).

Kits and Systems

This invention also provides kits and systems for use in practicing the methods described herein. For example, kits and systems for practicing the such methods may include one or more pharmaceutical compositions, which include one or both of the echinocandin antifungal agent and the glycopeptide antibacterial agent. For example, in certain embodiments, the kits may include a single pharmaceutical composition, present as one or more unit dosages, where the composition comprises both the echinocandin antifungal agent and the glycopeptide antibacterial agent. In yet other embodiments, the kits may include two or more separate pharmaceutical compositions, each containing either a echinocandin antifungal agent or a glycopeptide antibacterial agent.

In addition to the above components, the kits may further include instructions for practicing the methods of this invention. These instructions may be present in the kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means for providing instructions may be present in the kits.

The term "system" as used herein means a collection of an echinocandin antifungal agent and a glycopeptide antibacterial agent, present in a single or disparate composition, that are brought together for the purpose of practicing the methods of this invention. For example, separately obtained echinocandin antifungal agent and glycopeptide antibacterial agent dosage forms brought together and co-administered to a subject in need of treatment, according to the present invention, are a system according to the present invention.

Utility

The methods, compositions, kits and systems of this invention are useful for treating a subject having a fungal infection or medical condition which is caused by a pathogenic organism, e.g., a fungus, that is inhibited by or treatable with an echinocandin antifungal agent. In this regard, the subject may already have a fungal infection or the combination of an echinocandin antifungal agent and a glycopeptide antibacterial agent may be used in prophylactic therapy and empirical therapy where treatment is initiated prior to the identification of the causative pathogen.

A variety of subjects or patients or hosts are treatable using the methods, compositions, kits and systems of the present invention. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In a particular embodiment of interest, the subject or patient is a human.

Representative fungal conditions that may be treated according to the subject methods are those caused by the following pathogenic species: *Candida* spp., such as *C. albicans, C. glabrata, C. tropicalis, C. guilliermorulii, C. haemulonii, C. krusei, C. parapsilosis, C. lusitaniae, C. norvegensis, C. viswanathii,* and *C. kefyr*; Hyaline molds, such as *Aspergillus fumigatus, A. flavus, A. niger, A. terreus, Geotricium candidum; Pseudallescheria boydii, Histoplasma capsulatum* (var. *capsulatum*), *Coccidioides immitis, Cryptococcus bidus, C. Iaurentii,* and *C. fusarium*, as well as Mucormycotic organisms, e.g., *Zygomycetes* spp.; such as *Rhizopus pusillus, Cunninghamelle bertholletiae, Saksenaea vasiformis, Mucor ramosissimus, Absidia corymbifera, Apophysomyces elegans, Cokeromyces recurvatus,* and *Syncephalastrum racemosum.*

Accordingly, the present invention provides a method of treating a fungal infection in a subject, the method comprising administering to the subject an antifungal amount, e.g., an amount effective to treat the subject, of an echinocandin antifungal agent and a glycopeptide antibacterial agent as further described herein.

The compositions of this invention may also be used for coating of medical instruments or implants, agricultural applications, etc. as described further, for example, in U.S. Pat. No. 6,541,506.

In certain embodiments, the subject being treated suffers from both a fungal infection and a bacterial infection, where the bacterial infection is responsive to the glycopeptide antibacterial agent employed in this invention. Accordingly, this invention also provides a method for treating a bacterial infection and a fungal infection in a subject in need of treatment, the method comprising administering to the subject an antifungal amount of an echinocandin antifungal agent and an antibacterial amount of a glycopeptide antibacterial agent as further described herein.

Representative bacterial infections or medical conditions that may be treated include those caused by the following: *staphylococci*, including methicillin-resistant *staphylococci* and severe staphylococcal infections, such as staphylococcal endocarditis and staphylococcal septicemia; *enterococci*, including vancomycin-resistant *enterococci* (VRE); *streptococci*, including penicillin-resistant *pneumoniae* (PRSP); severe streptococcal infection, such as hospital and community acquired pneumonia (HAP and CAP); otitis media; and the like.

The utility of present invention is further illustrated by the following representative Examples.

EXAMPLES

The following examples are offered to illustrate this invention and are not to be construed in any way as limiting the scope of this invention. In the examples below, the following abbreviations have the following meanings unless otherwise indicated. All other abbreviations have their generally accepted meaning.

| | |
|---|---|
| CFU/mL | colony-forming units/milliliter |
| DMSO | Dimethyl sulfoxide |
| FIC | fractional inhibitory concentration |
| FICI | fractional inhibitory concentration index |
| NCCLS | National Committee for Clinical Laboratory Standards |
| MIC | minimum inhibitory concentration |
| MOPS | (3-[N-Morpholino]propanesulfonic acid) |
| OD | optical density |
| PDA | Potato Dextrose Agar |
| SDA | Sabouraud Dextrose Agar |

Example 1

Assay for Determining MIC and FICI

The following assay was used to determine the minimum inhibitory concentration (MIC) and fractional inhibitory concentration index (FICI) for combinations of antifungal agents and antibacterial agents. This assay and methods for calculating FICI are well known in the art. See, for example, Eliopoulos, E. G. and R. Moellering, Jr. "Antimicrobial Combinations" in *Antibiotics in Laboratory Medicine*, edited by V. Lorian, 4th Ed., Williams & Wilkins, Baltimore, Md., pp. 330-396 (1996); Shalit et al., Antimicrobial Agents and Chemotherapy 47(4):1416-1418 (2003); or Afeltra et al., Antimicrobial Agents and Chemotherapy 46(10):3323-3326 (2002).

FICI values are typically evaluated using the following criteria:

| | |
|---|---|
| FICI $\leq$ 0.5 | Synergistic effect |
| 0.5 < FICI < 1.0 | Additive effect |
| 1.0 < FICI < 4.0 | Indifferent effect |
| FICI > 4.0 | Antagonistic effect |

In this assay, a combination of an antifungal agent and a glycopeptide antibacterial agent was considered to be more effective than the antifungal agent alone, if the combined compounds demonstrated either a calculated FICI of less than or equal to about 0.5 or a decrease of the antifungal MIC by at least a one-fold dilution factor.

A. Fungal Strains

The fungal strains used in this assay are highly infectious. Standard safety measures, such as use of disposable screw cap tubes and use of safety masks, were strictly followed. All work was conducted in a Biosafety Level 2 cabinet. All materials and equipment (e.g., pipefters and incubators) were decontaminated between experiments.

The fungal strains used in this assay were obtained from the American Type Culture Collection (ATCC), Manassas, Va. In the table below, the ATCC deposit number for each strain is indicated under the column heading "ATCC". Other strains can be used if desired.

| | ATCC | Source/Description |
|---|---|---|
| Yeasts Strains | | |
| *Candida albicans* | 24433 | Nail infection |
| *Candida parapsilosis* | 22019 | Case of spruce, Puerto Rico |
| *Candida tropicalis* | 750 | Patient with bronchomycosis |
| *Candida krusei* | 32672 | Human, New Zealand |
| *Candida glabrata* | 200918 | Human tongue, Santa Rosa, California |
| *Cryptococcus neoformans* | 56991 | Human, Zaire |

-continued

| | ATCC | Source/Description |
|---|---|---|
| Hyaline Molds Strains | | |
| *Aspergillus fumigatus* | 14110 | Human sputum |
| *Aspergillus flavus* | 64025 | Human sputum, Ohio |
| *Fusarium moniliforme* | 38159 | Human, California |
| *Geotricium candidum* | 62231 | Ulcer in human mouth |
| *Pseudallescheria boydii* | 36283 | Human brain abcess |
| *Zygomycetes* spp. Strains | | |
| *Mucor circinelloides* | 26759 | Torn wounds, human, Canada |
| *Rhizopus microsporus* | 14050 | Fatal human *Rhizopus* infection |

Procedures, protocols, supplies and equipment used in this assay follow the recommendations approved and published by the National Committee for Clinical Laboratory Standards (NCCLS), Wayne, Pa. as described in NCCLS 2003, "Reference Method for Broth Dilution Antimicrobial Susceptibility Tests for Bacteria that Grow Aerobically; Approved Standard" (NCCLS document M7-A6); NCCLS 2002, "Reference Method for Broth Dilution Antifungal Susceptibility Tests of Filamentous Fungi that Grow Aerobically; Approved Standard" (NCCLS document M38-A); and NCCLS 2002 "Reference Method for Broth Dilution Antifungal Susceptibility Tests of Yeast; Approved Standards-2nd Edition" (NCCLS document M27-A2).

B. Test Compounds and Sources

The following semi-synthetic glycopeptide antibiotic was tested in this assay:

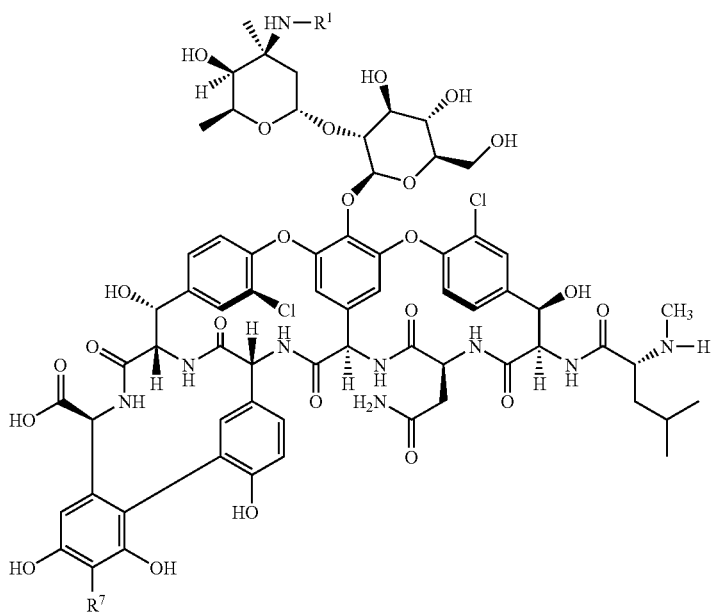

wherein $R^1$ and $R^7$ are as defined as follows:

| | $R^1$ | $R^7$ |
|---|---|---|
| Compound 1 | —CH$_2$CH$_2$—NH—(CH$_2$)$_9$CH$_3$ | —CH$_2$—NH—CH$_2$—P(O)(OH)$_2$ |

Compound 1, also known as telavancin, was prepared as described in Example 2 of U.S. Pat. No. 6,635,618 B2. Vancomycin was purchased from Sigma-Aldrich (St. Louis, Mo.).

Miconazole was purchased from U.S. Pharmacopeia (Rockville, Md.). Fluconazole, voriconazole (formulated as VFEND®) and caspofungin acetate (formulated as CANCIDAS®) were purchased from Peninsula Pharmacy (Burlingame, Calif.). Fluconazole was purchased as DIFULCAN® (oral formulation) and purified prior to use.

An initial stock of each compound was made in an appropriate solvent, i.e., either a DMSO solution for Compound 1, vancomycin and fluconazole; or a sterile water solution according to the instructions of the supplier for voriconazole and caspofungin.

C. Dilution Ratios

Using a checkerboard method, a 2-fold dilution 100× final concentration master plate was prepared using a 96-well U-shape microtiter plate and an appropriate solvent. In the "checkerboard" method, a microtiter plate is divided into "columns" in which each well in the column contains the same amount of an antifungal agent (Compound A) being diluted along the x-axis, and "rows" in which each well in the row contains the same amount of a glycopeptide antibacterial agent (Compound B) being diluted on the y-axis. Also included is a row (or column) for Compound A or B alone. The dilutions used in the checkerboard are exponential (by powers of two). The result is that each well in the microtiter plate contains a unique concentration of the two compounds being tested.

A matrix 2× final concentration was performed by transferring 30 µL of 100× Compound A and Compound B into a 1,440 µL RPMI in deep wells (one deep well per drug combination). After mixing, 100 µL of 2× drug combinations were distributed into 96-well microtiter plates. Compound A was diluted from Column 1 starting at 1,600 µg/mL to Column 11 (1.6 µg/mL). Wells in Column 1 contained a final concentration (after inoculum was added) of 16 µg/mL of Compound A; wells in Column 2 contained a final concentration of 8 µg/mL of Compound A; wells in Column 3 contained a final concentration of 4 µg/mL of Compound A; etc. Compound A was not added to Column 12, so Column 12 contained only Compound B.

Compound B was diluted from row A starting at 6,400 µg/mL down to row G (100 µg/mL). Wells in Row A contained a final concentration of 64 µg/mL of Compound B; Row B contained a final concentration of 32 µg/mL of Compound B; Row C contained a final concentration of 16 µg/mL of Compound B; etc. Compound B was not added to Row H, so Row H only contained Compound A.

Shown below is an example of a 96-well microtiter plate format used with combined Compound A and Compound B. Concentrations noted on the rows and columns are the final ones after inoculum were mixed with the combined compounds.

| Compound B (µg/mL final) | | Compound A (µg/mL final) | | | | | | | | | | | Compound B (µg/mL final) | |
|---|---|---|---|---|---|---|---|---|---|---|---|---|---|---|
| | | 16 | 8 | 4 | 2 | 1 | 0.5 | 0.25 | 0.125 | 0.063 | 0.031 | 0.015 | 0 | |
| | | 1 | 2 | 3 | 4 | 5 | 6 | 7 | 8 | 9 | 10 | 11 | 12 | |
| 64 | A | | | | | | | | | | | | | A 64 |
| 32 | B | | | | | | | | | | | | | B 32 |
| 16 | C | | | | | | | | | | | | | C 16 |
| 8 | D | | | | | | | | | | | | | D 8 |
| 4 | E | | | | | | | | | | | | | E 4 |
| 2 | F | | | | | | | | | | | | | F 2 |
| 1 | G | | | | | | | | | | | | | G 1 |
| 0 | H | | | | | | | | | | | | | H 0 |
| | | 1 | 2 | 3 | 4 | 5 | 6 | 7 | 8 | 9 | 10 | 11 | 12 | |
| | | 16 | 8 | 4 | 2 | 1 | 0.5 | 0.25 | 0.125 | 0.063 | 0.031 | 0.015 | 0 | |

In most cases, MIC of the glycopeptide antibacterial compound alone was >64 µg/mL. In order to get an accurate measurement, a standard MIC assay using NCCLS protocols was performed with an extended concentration range of from 256 µg/mL to 0.25 µg/mL. The MIC of the glycopeptide antibacterial compound determined from this experiment was used in FIC calculations. If the MIC of the antibiotic compound was >256 µg/mL, FIC of the compound was calculated using 256 µg/mL as the closest value to the true MIC.

D. Media and Inoculum Preparation

RPMI-1640 without sodium bicarbonate media (GIBCO-BRL, Carlsbad, Calif.), an enriched media formulated for mammalian cells, was used according to the NCCLS guidelines for yeast and filamentous fungi susceptibility testing. The medium was buffered with 0.165 M 3-[N-morpholino] propanesulfonic acid (MOPS) supplemented with 20 g/L glucose and pH adjusted to 7.0 with hydrogen chloride. Sabouraud Dextrose Agar (SDA) slants and plates, and Potato Dextrose Agar (PDA) plates were purchased from Hardy Diagnostic (Santa Maria, Calif.).

Yeast cultures were started from −80° C. frozen stock streaked on SDA slants and incubated at 35° C. under aerobic conditions for 24 h. The slants were kept in the refrigerator for up to 2 weeks and used regularly as a starting culture. About 24 to 48 h before each assay was run, yeasts were streaked on SDA plates for isolated colonies. To prepare the inoculum, from one to four colonies were resuspended in 5 mL of saline, and vortexed for 15 sec.

Molds started from −80° C. frozen stocks were spotted in the center of the PDA plates. The plates were incubated at 35° C. for 7 days to induce conidiospores and sporangiospores. Fast growing molds (i.e., *Fusarium* spp. and *Rhizopus* spp.) were incubated at 35° C. for 48 to 72 h, then kept at 25-28° C. for up to 7 days. To prepare the inoculum, the mold spores were resuspended in saline (avoiding aerosol formation), then vortexed for 15 sec, and the hypheal particles were allowed to settle for 5 to 10 min.

The initial optical density (OD) at 530 nm of the vortexed cells suspended in saline was less than 0.5 as measured using a SmartSpec 3000 spectrophotometer (BioRAD, Hercules, Calif.). For most yeast and mold cultures, the optical density (OD) of the suspension was adjusted to 0.11 in saline to provide $\sim 0.4 \times 10^6$ CFU/mL. However, for *Fusarium moniliforme* and *Pseudallescheria boydii* the OD of the suspension was adjusted to OD=0.17 to provide $\sim 0.4 \times 10^6$ CFU/mL. Then the culture was diluted 1:1,000 for yeasts and 1:50 for molds in RPMI media (GIBCO-BRL) to get a 2× final inoculum. A final inoculum of $0.5 \times 10^3$ to $2.5 \times 10^3$ CFU/mL (yeasts) and $0.4 \times 10^4$ to $5 \times 10^4$ CFU/mL (molds) was used to ensure greater reproducibility of test results.

Using an 8-channel multipipetter, 100 µL of the 2× inoculum was added to 100 µL of 2× drug dilution starting from the lowest dilution to the highest. Microtiter plates were incubated at 35° C. under aerobic conditions for 48 h before reading the results. Plates were read after about 24 h (*Rhizopus* spp.) or 72 h (*Cryptococcus neoformans*).

Additionally, for validation purposes (i.e., to confirm the accuracy of the pipetted inoculum amount and the viability of cells) 100 µL of the inoculum was plated on a separate SDA plate. If, after about 46 to about 48 hours, the inoculum size calculated from the colony count on the validation plate was outside the expected range of $0.5 \times 10^3$ to $2.5 \times 10^3$ CFU/mL (yeasts) and $0.4 \times 10^4$ to $5 \times 10^4$ CFU/mL (molds), the entire assay test was redone.

After about 46 to about 48 hours, the growth of the fungus in the 96-well microtiter plates was evaluated and the minimum inhibitory concentration (MIC) and fractional inhibitory concentration (FIC) were calculated.

Each column and row of the microtiter plates was visually assessed for cell growth, which manifested as clouding or turbidity of the media. RPMI media was clear and transparent at inoculation. When no turbidity was observed, the growth of the inoculum cells was inhibited, and the well remained clear.

The minimum inhibitory concentration (MIC) of a compound, i.e., the minimum inhibitory concentration of compound A ($MIC_A$), is the concentration of compound A at which no growth is observed.

E. Measurement of Synergy Effects

To measure the in vitro interactions of test compounds, the Fractional Inhibitory Concentration was calculated using the concentration that reduced the antifungal compound MIC by at least a 2-fold dilution factor (i.e., "concentration of compound in synergistic well"). The Fractional Inhibitory Concentration for compound A, FIC(A) is equal to the concentration of compound A in synergistic well divided by MIC(A). Similarly, for compound B, the FIC(B) is equal to the concentration of compound B in synergistic well divided by MIC(B). The Fractional Inhibitory Concentration Index (FICI) is equal to the sum of FIC(A)+FIC(B).

$$FIC(A) = \frac{\text{concentration } (A) \text{ in synergistic well}}{MIC(A)}$$

$$FIC(B) = \frac{\text{concentration } (B) \text{ in synergistic well}}{MIC(B)}$$

$$FICI = FIC(A) + FIC(B)$$

For each combination of test compounds, the assay was repeated at least twice to show reproducibility. Because MICs have an inherent 50% error associated with the assay, no average or statistical analysis was performed. FICs however are not affected by the MIC variability.

The calculated value for the FICI of the combined test compounds was compared to the following standards in certain embodiments:

| FICI ≦ 0.5 | synergistic effect |
|---|---|
| FICI > 0.5 | nonsynergistic effect |

The interactions of the combined compounds can be expressed as a graph in which antifungal MIC (μg/mL) is plotted on the Y-axis as a function of antibacterial concentration (μg/mL) which is plotted on X-axis. If desired, the synergistic interaction of the two combined compounds can alternatively be calculated or validated with other assays, such as a time-kill synergy assay as discussed in Eliopoulos, E. G. and R. Moellering, Jr.

F. Results and Discussion

The results of the assays are shown in Tables 1, 2 and 3.

TABLE 1

FICI for Combinations of Glycopeptide Antibacterial Agents and Caspofungin

| | FICI | |
|---|---|---|
| Fungal Strains | Compound 1 | Vancomycin |
| C. albicans ATCC 24433 | 0.27 | 2.00 |
| C. parapsilosis ATCC 22019 | 0.38 | 2.00 |
| C. tropicalis ATCC 750 | 0.26 | 2.00 |
| C. krusei ATCC 32672 | 0.31 | 2.00 |
| C. glabrata ATCC 200918 | 0.28 | 2.00 |

TABLE 2

FICI for Combinations of Compound 1 and Caspofungin

| Fungal Strains | FICI |
|---|---|
| C. albicans ATCC 24433 | 0.27 |
| C. parapsilosis ATCC 22019 | 0.38 |
| C. tropicalis ATCC 750 | 0.26 |
| C. krusei ATCC 32672 | 0.31 |
| C. glabrata ATCC 200918 | 0.28 |
| C. neoformans ATCC 56991 | 0.75 |
| A. fumigatus ATCC 14110 | 0.28 |
| A. terreus ATCC 46941 | 0.31 |
| A. flavus ATCC 64025 | 0.16 |
| F. moniliforme ATCC 38159 | 2 |
| S. prolificans ATCC 200543 | 1.25 |
| P. boydii ATCC 38283 | 0.31 |
| G. candidum ATCC 62231 | 0.31 |
| M. circinelloides ATCC 26759 | 2 |
| R. miscrosporus ATCC 14050 | 2 |

TABLE 3

FICI for Combinations of Compound I and Azole Antifungal Agents

| | FICI | | |
|---|---|---|---|
| Fungal Strain | Fluconazole | Miconazole | Voriconazole |
| C. albicans ATCC 24433 | 2.00 | 2.00 | Not Applicable |
| C. parapsilosis ATCC 22019 | 2.00 | 2.00 | Not Applicable |
| C. tropicalis ATCC 750 | 2.00 | 2.00 | Not Applicable |
| C. krusei ATCC 32672 | 2.00 | Not Determined | 1.13 |
| C. glabrata ATCC 200918 | 2.00 | Not Determined | 1.13 |

The data in Tables 1, 2 and 3 demonstrate that combinations of an echinocandin antifungal agent, such as caspofungin, and a glycopeptide antibacterial agent having a substituent comprising at least about 8 carbon atoms, such as telavancin, typically have a synergistic or additive effect against various strains of fungi. For example, the combination of Compound 1 and caspofungin was synergistic against all yeast strains tested, except C. neoformans against which caspofungin has no activity.

In contrast, the combination of vancomycin and caspofungin was not synergistic or additive. Moreover, azole antifungal agents did not show a synergistic or additive effect when combined with the glycopeptide antibacterial agents.

These results clearly demonstrate that the present invention provides significant advantages for administering an echinocandin antifungal agent to a subject in need thereof. More specifically, by administering such an echinocandin antifungal agent in combination with a specified glycopeptide antibacterial agent, the efficacy of the echinocandin antifungal agent is significantly increased thereby allowing for reduced dosages (e.g., to reduce or eliminate toxicity), quicker treatment protocols, etc.

While the present invention has been described with reference to specific aspects or embodiments thereof, it will be understood by those of ordinary skill in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A method for administering an echinocandin antifungal agent to a subject having a fungal infection, the method comprising:
    administering to the subject an echinocandin antifungal agent selected from caspofungin or a pharmaceutically acceptable salt thereof; and a glycopeptide antibacterial agent selected from telavancin or a pharmaceutically acceptable salt thereof;
    wherein the fungal infection is caused by *Candida albicans, Candida parapsilosis, Candida tropicalis, Candida krusei, Candida glabrata, Aspergillus fumigatus, Aspergillus terreus, Aspergillus flavus, Pseudallescheria boydii, Geotricium candidum*, or a combination thereof.

2. The method according to claim 1, wherein the echinocandin antifungal agent and the glycopeptide antibacterial agent are administered sequentially.

3. The method according to claim 1, wherein the echinocandin antifungal agent and the glycopeptide antibacterial agent are administered simultaneously.

4. A method for treating a fungal infection in a subject, the method comprising:
    administering to the subject an antifungal amount of an echinocandin antifungal agent selected from caspofungin or a pharmaceutically acceptable salt thereof; and a glycopeptide antibacterial agent selected from telavancin or a pharmaceutically acceptable salt thereof;
    wherein the fungal infection is caused by *Candida albicans, Candida parapsilosis, Candida tropicalis, Candida krusei, Candida glabrata, Aspergillus fumigatus, Aspergillus terreus, Aspergillus flavus, Pseudallescheria boydii, Geotricium candidum*, or a combination thereof.

5. The method according to claim 4, wherein the echinocandin antifungal agent and the glycopeptide antibacterial agent are administered sequentially.

6. The method according to claim 4, wherein the echinocandin antifungal agent and the glycopeptide antibacterial agent are administered simultaneously.

7. A method for increasing the efficacy of an echinocandin antifungal agent, the method comprising administering the echinocandin antifungal agent selected from caspofungin or a pharmaceutically acceptable salt thereof; to a subject in combination with a glycopeptide antibacterial agent selected from telavancin or a pharmaceutically acceptable salt thereof;
    wherein the subject has a fungal infection caused by *Candida albicans, Candida parapsilosis, Candida tropicalis, Candida krusei, Candida glabrata, Aspergillus fumigatus, Aspergillus terreus, Aspergillus flavus, Pseudallescheria boydii, Geotricium candidum*, or a combination thereof.

8. The method according to claim 7, wherein the echinocandin antifungal agent and the glycopeptide antibacterial agent are administered sequentially.

9. The method according to claim 7, wherein the echinocandin antifungal agent and the glycopeptide antibacterial agent are administered simultaneously.

* * * * *